US009993396B2

(12) United States Patent
Sattig et al.

(10) Patent No.: US 9,993,396 B2
(45) Date of Patent: Jun. 12, 2018

(54) BONE CEMENT AND A METHOD FOR PRODUCING SAME

(71) Applicant: AAP BIOMATERIALS GMBH, Dieburg (DE)

(72) Inventors: Christoph Sattig, Dieburg (DE); Elvira Dingeldein, Darmstadt (DE)

(73) Assignee: AAP BIOMATERIALS GMBH, Dieberg (DE)

( * ) Notice: Subject to any disclaimer, the term of this patent is extended or adjusted under 35 U.S.C. 154(b) by 0 days. days.

(21) Appl. No.: 14/527,872

(22) Filed: Oct. 30, 2014

(65) Prior Publication Data

US 2015/0051305 A1 Feb. 19, 2015

Related U.S. Application Data

(62) Division of application No. 13/499,348, filed as application No. PCT/EP2010/005951 on Sep. 30, 2010, now abandoned.

(30) Foreign Application Priority Data

Sep. 30, 2009 (DE) .......................... 10 2009 043 550

(51) Int. Cl.

| A61L 24/02 | (2006.01) |
|---|---|
| A61L 24/06 | (2006.01) |
| A61K 6/087 | (2006.01) |
| A61L 24/00 | (2006.01) |
| A61L 27/46 | (2006.01) |
| A61L 27/56 | (2006.01) |
| A61L 27/58 | (2006.01) |

(52) U.S. Cl.
CPC .......... *A61K 6/087* (2013.01); *A61L 24/0036* (2013.01); *A61L 24/0042* (2013.01); *A61L 24/0084* (2013.01); *A61L 27/46* (2013.01); *A61L 27/56* (2013.01); *A61L 27/58* (2013.01); *A61L 2300/406* (2013.01); *A61L 2430/02* (2013.01)

(58) Field of Classification Search
USPC ................................. 523/116, 333; 524/127
See application file for complete search history.

(56) References Cited

U.S. PATENT DOCUMENTS

| 4,093,576 A | * | 6/1978 | deWijn ................... A61L 24/06 433/173 |
| 5,650,108 A | * | 7/1997 | Nies .................... A61L 24/0036 264/109 |
| 5,814,681 A | * | 9/1998 | Hino .................... A61L 24/0084 222/145.5 |
| 8,173,721 B2 | * | 5/2012 | Lavergne ............ A61L 24/0094 523/115 |
| 8,357,364 B2 | * | 1/2013 | Kumta .................... A61K 33/06 424/93.7 |
| 8,487,021 B2 | * | 7/2013 | Truckai .................. A61K 31/78 523/116 |
| 2002/0115742 A1 | | 8/2002 | Trieu et al. |
| 2006/0199876 A1 | * | 9/2006 | Troczynski ............. A61L 27/32 523/115 |
| 2010/0185299 A1 | * | 7/2010 | Nies ........................ A61L 27/04 623/23.53 |

FOREIGN PATENT DOCUMENTS

| CN | 1810300 A | 8/2006 |
| DE | 10339953 B3 | 4/2005 |
| EP | 0664133 B1 | 7/1995 |
| EP | 0938449 B1 | 9/1999 |
| EP | 1317261 B1 | 6/2003 |
| EP | 1351721 B1 | 4/2007 |
| WO | WO2010095001 | * 8/2010 |

OTHER PUBLICATIONS

German Office Action dated Jan. 9, 2015 corresponding to German Patent Application No. 10 2009 043 550.6 with English translation, 13 pages.
English translation of International Search Report dated May 17, 2011 corresponding to International Patent Application No. PCT/EP2010/005951, 3 pages.
English translation of International Preliminary Report on Patentability dated Apr. 3, 2012 corresponding to International Patent Application No. PCT/EP2010/005951, 9 pages.
English translation of Written Opinion of International Searching Authority dated May 17, 2011 corresponding to International Patent Application No. PCT/EP2010/005951, 8 pages.
Beruto, D. T., et al., "Use of [alpha]-tricalcium phosphate (TCP) as powders and as an aqueous dispersion to modify processing, microstructure, and mechanical properties of polymethylmethacrylate (PMMA) bone cements and to produce bone-substitute compounds," Journal of Biomedical Materials Research, Univ. of Genoa, Genoa, Italy, Mar. 2000, pp. 498-505.

* cited by examiner

*Primary Examiner* — Tae H Yoon
(74) *Attorney, Agent, or Firm* — Ohlandt, Greeley, Ruggiero & Perle, L.L.P.

(57) ABSTRACT

The present disclosure relates to a bone cement composed of a hydrophilic component and a hydrophobic component, wherein biodegradable material is deposited in pores of the bone cement via the hydrophilic component.

12 Claims, 4 Drawing Sheets

BONE CEMENT AND A METHOD FOR PRODUCING SAME

CROSS-REFERENCE TO RELATED APPLICATION

The present application is a divisional application of U.S. application Ser. No. 13/499,348, filed on Jul. 19, 2012,now abandoned, which is in turn a national stage application under 35 U.S.C. § 371 of International Patent Application No. PCT/EP2020/005951, filed on Sep. 30, 2010, each of which is incorporated in its entirety by reference.

BACKGROUND OF THE DISCLOSURE

1. Field of the Disclosure

The disclosure relates to a bone cement and a method for producing same.

2. Description of the Related Art

Different types of bone cement are known from practice. In order to provide a biodegradable bone cement, i.e., a bone cement that is replaced over time after it is applied by new growth of bone tissue, bone cements based on calcium phosphate or calcium sulfate, for example, are known. After they are applied in each case, a sufficient initial stability can be achieved with these bone cements. Of course, the hardened material is very brittle, so that a sufficient permanent stability cannot be achieved for many cases of application. Calcium phosphates are also known. Of course, in the case of calcium phosphate-based bone cements, there is a softening of the material even after a short time, so that in many cases, defect sites cannot be stabilized sufficiently rapidly, particularly in elderly patients. Bone cements based on calcium sulfate or calcium phosphate-are generally not suitable for the anchoring of dynamic load-bearing implants.

For these applications, acrylic-based bone cements are generally used, and not only in elderly patients. These have the advantage of a high rigidity even after a brief hardening or curing. For the most part, a connective-tissue type of layer is formed around the implanted acrylic-based cement; bone material does not grow into the bone cement, but an acrylic-based bone cement is usually very well tolerated.

Acrylic-based bone cements generally cannot be degraded by the body. Therefore, attempts have been made to improve the biocompatibility of these types of cements, for example, by addition of hydroxyapatite. These types of additives for the most part, of course, are only accessible at the surface of the cement, predominantly surrounded by acrylic and for the most part are not resorbable. Finally, the known additive of calcium compounds can usually only improve the growth of tissue on the bone cement, but the quantity of accessible particles is usually not sufficient to achieve or to promote a new formation of bone in direct contact. Further, the opinion is offered that particularly in the case of vertebroplastic and kyphoplastic applications, the addition of calcium compounds is accompanied by disadvantages, since the E-modulus is increased based on the added particles, which can act negatively on the adjacent bone, in particular on the adjacent vertebral body. The danger of fracture that exists, without anything further, with the use of relatively solid acrylic-based bone cements thus may in fact be increased by the addition of hydroxyapatite particles.

SUMMARY OF THE DISCLOSURE

In comparison to this, the disclosure relates to an acrylic-based bone cement, in which the named disadvantages of known acrylic-based bone cements will be reduced.

In particular, an object of the disclosure is to provide a bone cement that is at least partially biodegradable and therefore natural bone tissue can grow through it. In addition, the bone cement will be able to be better adapted in its strength to the strength of natural bone, whereby, in particular, the danger of fractures in the vertebral region will be reduced.

The object of the disclosure will be achieved by a bone cement, a cured bone cement, as well as by a method for mixing bone cement according to one of the independent claims. Preferred embodiments and enhancements of the disclosure can be taken from the respective subclaims.

Thus, in one embodiment, the present disclosure provides a method for mixing a bone cement. The method comprises the step of mixing a polymerizable hydrophobic component with a hydrophilic, highly viscous, and dimension stable paste to form a mixture, wherein the paste comprises a biodegradable material, so that the paste forms open-pore regions within the hydrophobic component, and wherein the biodegradable material is within the open-pore regions. The method further comprises curing the mixture, to form the bone cement.

DETAILED DESCRIPTION OF THE DISCLOSURE

Figure 1:
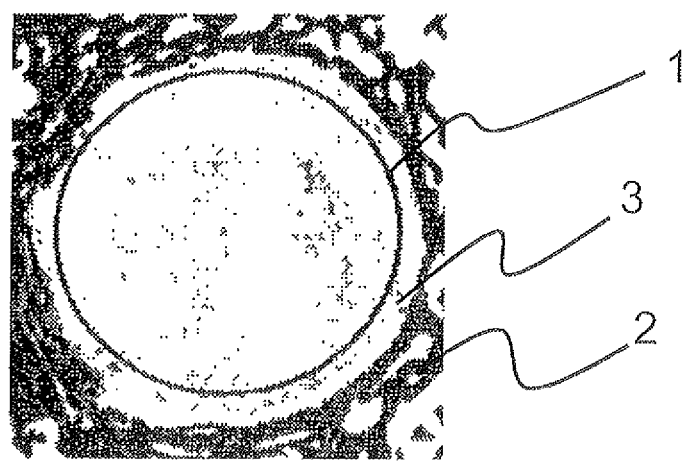
FIGS. 1 and 2 show schematically the histological findings for the femoral condyles of a sheep, which were produced as follows.

The disclosure relates to a bone cement that is provided particularly for inserting prostheses, but also for closing or filling bone defects, depending on the indication in each case.

The bone cement comprises at least one polymerizable hydrophobic component, at least one hydrophilic component and biodegradable particles.

Understood as a hydrophilic component and a hydrophobic component are two components that are immiscible, due to their hydrophilic or hydrophobic properties. The hydrophilic component preferably comprises water, the biodegradable particles forming a suspension in water. When the bone cement is mixed by means of a suitable stirring device, the aqueous, hydrophilic component does not mix with the hydrophobic component, so that the biodegradable particles remain behind in the pores formed by the hydrophilic component. Unlike the addition of biodegradable particles as pure additives to the polymer compound, the biodegradable particles are thus freely accessible. In the sense of the disclosure, it is understood that "immiscible" does not mean that a part of the hydrophilic component or a part of the water cannot dissolve in the hydrophobic component, particularly in the polymer. Thus, certain acrylates absorb up to 10% water. In the case of a suitably sized quantity of water, it is assured, however, that there is always sufficient water as the hydrophilic component that is immiscible with the polymer.

In a preferred embodiment of the disclosure, at least 50, preferably at least 80% of the biodegradable particles are contained in the hydrophilic component. A large portion of the particles is thus freely accessible. Unlike known bone cements with biodegradable particles as an additive, the particles are not sealed by the polymer matrix.

The hydrophobic component comprises an acrylate monomer, in particular, an acrylate monomer being understood as a compound that can be polymerized into a polyacrylic. The latter involves an acrylic-based bone cement. For example, it may involve an acrylic acid ester, in particular methyl methacrylate. Monomers or oligomers from which polyacrylates form are sufficiently known and are hydrophobic, at least in the unhardened state, so that when they are combined with water, usually they do not produce dispersions with a fine distribution. In the hardened or cured state, acrylate-based bone cements usually reduce their hydrophobic properties and can in fact absorb water up to several percent of their weight. According to the disclosure, the hydrophobic properties need only be present in the unhardened state; therefore, a dissolution or a fine dispersion of the two components does not occur.

Rather, at least partially open-pore regions, which are first filled with the hydrophilic component, are formed by the hydrophilic component. The biodegradable particles, which are preferably contained in the hydrophilic component, are predominantly accumulated in the pores, so that after curing, an at least partially open-pore cured acrylic cement is present, the pores of which are occupied by biodegradable material.

Based on the open pores, natural bone tissue can grow into the hardened bone cement, this ingrowth being considerably accelerated by the biodegradable particles.

The inventors could thus provide an acrylic-based bone cement, which can be interspersed with natural bone material after its application.

Further, the inventors have discovered that the addition of a hydrophilic component, in particular the addition of water, reduces the E-modulus and simultaneously increases the yield strength at break. In this way, in vertebroplasty and kyphoplasty or related applications, the danger of fractures of both cured bone cement and adjacent bone material can be reduced.

The biodegradable particles are preferably contained in the hydrophilic component. Theoretically, however, it would also be conceivable that biodegradable particles are added together with an acrylic-based bone cement powder or, in fact, with the acrylate monomer, since the biodegradable particles would predominantly migrate into the hydrophilic component based on their properties alone.

The hydrophilic component preferably comprises water and a calcium carbonate, sulfate and/or phosphate. Carbonate, sulfate, phosphate in this case are understood in the broadest sense, thus all compounds of sulfur, phosphorus and carbonates with calcium.

In particular, the hydrophilic component comprises hydroxyapatite. The biodegradable material, in particular the hydroxyapatite, is preferably present in nanoparticulate form, thus with an average particle size of less than 100 nm. When stabilizers are employed, larger particles, in particular having a size of up to 20 μm can also be used.

The particles are preferably present in a suspension, which, when mixed with the hydrophobic component, mostly sticks together and thus thread-like structures are formed, which lead to an interconnected structure. A viscous suspension of nanoparticles has these properties to a particular extent.

In particular, nanoparticulate hydroxyapatite is also particularly suitable for accelerating the ingrowth of bone tissue.

This type of hydroxyapatite as well as its production is described, for example, in European patents EP 0 664 133 B1, EP 0 938 449 B1 and EP 1 317 261 B1. With respect to the added particulate hydroxyapatite, reference is made to the full extent to the disclosure content of these documents. In particular, hydroxyapatite particles or suspensions containing hydroxyapatite particles as they are described in one of the named documents are used.

In an enhancement of the disclosure, the hydrophilic component contains a substance that starts a polymerization of the hydrophobic component, in particular an initiator. Thus, the bone cement can be provided as a two-component system, in which the initiator is contained in the hydrophilic component. In particular, dibenzoyl peroxide can be used as an initiator.

In a preferred embodiment of the disclosure, the hydrophobic component contains polymer particles. Usually bone cement is provided as a combination of monomer and powder. Thus the mixed bone cement can be provided with a paste-like consistency. The polymer particles are usually partially dissolved during the curing and are bound in the forming polymer matrix. Due to the fact that the complete volume need not be polymerized, heating is also reduced during the curing.

Also, the hydrophilic component reduces the evolution of heat during curing of the bone cement according to the disclosure, which presents an additional advantage of the bone cement according to the disclosure.

In an enhancement of the disclosure, the bone cement contains an x-ray contrast agent. The x-ray contrast agent in this case can be contained in the hydrophilic component and/or in the hydrophobic component.

In another enhancement of the disclosure, the bone cement contains a pharmaceutically active substance, in particular an antibiotic. The antibiotic is preferably contained in the hydrophilic component.

In a preferred embodiment of the disclosure, the bone cement contains between 10 and 50% biodegradable material, in particular biodegradable particles, between 20 and 80% of the polymerizable hydrophobic component, optionally between 10 and 60% polymer particles and between 2 and 30% water (unless otherwise indicated, the data are always in weight %).

In addition, the disclosure relates to a bone cement, in particular having one or more of the above features, which comprises a polymer component as well as a liquid that is immiscible with the polymer component. The liquid involves water in particular. According to the disclosure, biodegradable particles are contained in the liquid that is immiscible with the polymer component. In particular, the biodegradable particles are present as a suspension in water. The polymer component particularly involves a monomer or a prepolymer that hardens into a polymer matrix. In order to accelerate curing and to reduce the evolution of heat, the polymer component usually also comprises polymer particles that are mixed in during mixing with the monomer.

It particularly involves an acrylate-based bone cement. The polymer component is immiscible with the suspension in which the biodegradable particles are contained. Due to the inclusion of drops of the suspension in this case, pores are formed, in which the biodegradable particles are freely accessed.

It has turned out that during the formation of pores, longitudinally drawn-out, channel-shaped recesses are formed at least partially, so that a polymer matrix with interconnecting pores is formed.

In addition, the disclosure relates to a bone cement, comprising 25 to 80% polymeric bone cement powder, 5 to 30% water, 10 to 70% biodegradable particles, as well as a monomer and an initiator.

In addition, the disclosure relates to a cured bone cement, in particular a bone cement that is cured from the above-described bone cement. The cured bone cement comprises a polymer backbone with open pores that are filled at least partially with biodegradable material. In particular, it involves a cured acrylate-based bone cement, whose polymer backbone comprises an acrylate, in particular a polymethylmethacrylate.

In particular, an acrylate-based bone cement, which has in the cured state an E-modulus of less than 4500 MPa, preferably less than 2000 MPa, and particularly preferred, less than 1600 MPa, can be provided by the disclosure. In the sense of the disclosure, the E-modulus is measured in the initially cured state after a curing time of approximately five hours by application of ISO5833:2002 Annex F. The desired rigidity can be adjusted via the ratio of hydrophobic and hydrophilic components with the bone cement according to the disclosure.

The bone cement according to the disclosure is thus relatively soft for an acrylate-based bone cement, which reduces the danger of subsequent fractures after treatment of vertebral bodies.

In a preferred embodiment, the cured bone cement has a porosity between 5 and 90, preferably between 10 and 50, and particularly preferred between 10 and 35% referred to the polymer backbone. In the sense of the Application, porosity is understood to be the calculated porosity, in which closed pores are also included in the porosity. In contrast, the hydrophilic component and the biodegradable material, which is found in the hydrophilic component, are not included in the porosity.

In the sense of the disclosure, porosity is particularly understood to be the calculated porosity, for which the volume of the hydrophobic component from which the polymer backbone is formed, is placed in a ratio with the volume of the hydrophilic component.

In one embodiment of the disclosure, the cured bone cement has an average pore size between 5 μm and 5 mm, preferably between 20 and 200 μm. The pore size can be controlled, among other things, by selection of the mixing method. It is also conceivable to reduce the pore size by additives that reduce the surface tension of water.

In an enhancement of the disclosure, the polymer backbone is at least partially composed of a cross-linked polymer. In particular, polymer particles of a partially cross-linked polymer can be used for producing the bone cement. After adding the monomer, portions that are not cross-linked are partially dissolved and can serve as a connecting link to the polymer matrix forming as the monomer. Thus, particles are not only embedded, but are cross-linked to the molecular plane.

In addition, the disclosure relates to a method for producing bone cement, wherein a polymerizable hydrophobic component is mixed with a hydrophilic component and biodegradable material.

At least partially open-pore regions, which are first filled with the hydrophilic component, are formed by the hydrophilic component, which by definition is immiscible with the hydrophobic component. When the bone cement is used in vivo, the trapped water is usually replaced by body fluid and the remaining biodegradable particles that are found in the pores are freely accessible, which considerably improves ingrowth into the bone cement.

The biodegradable material is preferably added and mixed together with the hydrophilic component as a suspension, in particular as a paste. Preferably, the paste is highly viscous and essentially dimensionally stable, such as a curd or fresh cheese, for example. In particular, the viscosity can amount to between 1 and 100,000 Pa·s.

When a suspension containing nanoparticles that have been produced in the suspension is used, such as nanoparticulate hydroxyapatite for example, 20 to 40% particles in the suspension lead to the desired consistency.

If the particles are introduced as a powder or if precipitated particles are used, the particle concentration usually must be higher in order to obtain the desired consistency. Precipitated material containing particles that are clearly larger than 100 nm can therefore make necessary a particle fraction of 60% or more in the suspension.

It is a decisive factor that the hydrophilic component is neither sedimented nor independently separated from the hydrophobic component. Therefore, a "street"-like structure remains at least partially, which is filled with a particle suspension.

Unlike known acrylic-based bone cement containing hydroxyapatite, the biodegradable particles are highly accessible and promote the ingrowth into the cured cement.

It is particularly provided that a concentrated suspension having calcium-containing particles be used.

Due to the consistency of the hydrophilic component and/or the hydrophobic component and due to their ratio to one another, both the degree of porosity as well as the size of the pores, and within certain limits, also the appearance of the pores, particularly the pores formed as channels, can be determined in advance.

The hydrophilic component present as the suspension preferably has a viscosity that is similar to the remaining bone cement.

The components can be mixed with one another by means of a statistical mixer, which leads to particularly good results when two pastes are employed.

In a preferred embodiment of the disclosure, it is provided that in the mixing, at least two pastes are employed, a first paste containing the polymerizable hydrophobic component and the second paste containing the biodegradable material, an initiator and water.

The bone cement according to the disclosure can thus be used as a two-component system.

The first paste is preferably mixed with an accelerator, which accelerates the polymerization. Dimethyl-p-toluidine, in particular, is used as the accelerator.

The use of a pre-polymerized, partially cross-linked polymer, for example in the form of a pearl polymer, after mixing with the monomer, leads to the partial dissolution of the polymer particles and the formation of long-chain polymers of the acrylate monomer is accelerated. Simultaneously, partially dissolved or dissolved-out components of the polymer particles lead to a thickening of the mixture to produce the desired viscosity.

In order to stabilize the monomer, for example, hydroquinone can be added, which prevents a premature polymerization due to radical scavenging.

In an enhancement of the disclosure, a polymerizable metal salt is used for producing the hydrophobic component. In particular, zirconium (meth)acrylate or barium (meth)acrylate can be used. A metal acrylate, particularly a zirconium or barium acrylate, is preferably formed from the metal salt due to the presence of acrylic acid or methacrylic acid.

Cross-links can be provided via an acrylate, in particular a metal acrylate, which can be well dissolved in the hydrophobic component due to the good shielding of the metal atom. Both butylals and methylacrylates can be used.

In particular, the acrylate can be produced as a particulate prepolymer from an acetate by addition of methacrylic acid.

In particular, the acrylate can be produced from zirconium acetate. The acetate can be precipitated by means of methacrylic acid, and the zirconium acrylate that forms can be used for producing the hydrophobic component. Also, other acrylates, such as, for example, aluminum acrylate, magnesium acrylate and calcium acrylate, can be used. By the use of zirconium or barium acrylate, in particular, an x-ray contrast agent can likewise be bound in the polymer matrix. The use of titanium acrylate is also conceivable, in particular for the additional provision of an x-ray contrast agent.

A bone cement can be produced as follows, by way of example.

EXAMPLE 1

As a first step, an acrylate-based bone cement composed of a monomer and a polymeric bone cement powder are mixed. A bone cement paste is formed in this way, as it can be used according to the prior art.

After mixing this paste, another paste that is composed of a suspension of finely dispersed, distributed particles of hydroxyapatite, calcium carbonate, calcium sulfate and/or calcium phosphate are mixed and combined with the bone cement in a suitable mixing device. The paste that forms from the two pastes can now be used.

Instead of first producing the paste from acrylate-based bone cement in a separate step, a concentrated suspension containing hydroxyapatite, calcium carbonate, calcium sulfate and/or calcium phosphate can also be mixed directly with the polymer particles of the acrylate-based bone cement and the monomer.

EXAMPLE 2

In a first step, a paste composed of an aqueous phase and finely dispersed, distributed particles of hydroxyapatite, calcium carbonate, calcium sulfate and/or calcium phosphate and dibenzoyl peroxide is mixed with a second paste. Optionally, a pharmacologically effective substance is added. The second paste contains methyl(meth) acrylate and/or butyl acrylate as the monomer, dimethyl-p-toluidine as an accelerator and optionally, an x-ray contrast agent. Further, the second paste contains a partially cross-linked PMMA pearl polymer. The two pastes are mixed by means of a suitable mixer with or without a statistical mixing element and can then be introduced into defect sites by means of a syringe or by hand.

Due to the methyl methacrylate, the PMMA contained in the pearl polymer partially dissolves out from the beads or the beads swell and the otherwise very thin fluid methyl methacrylate is thickened. For additional thickening, other polymers, in particular PMMA polymers, dissolved or swollen polymers, can be mixed in.

The disclosure will be explained in the following in more detail with reference to FIG. 1 to FIG. 3 of the drawings.

A defect approximately 15 cm deep and 10 mm diameter was made by means of a drill in the medial femoral condyle of both hind limbs of a sheep, and on one side the defect was filled with conventional acrylate-based bone cement, and on the other side with a bone cement according to the disclosure. The animal was euthanized three months after the surgery. For the histological investigation, the condyles were sawed into slabs and stained bone sections were prepared.

Figure 2:
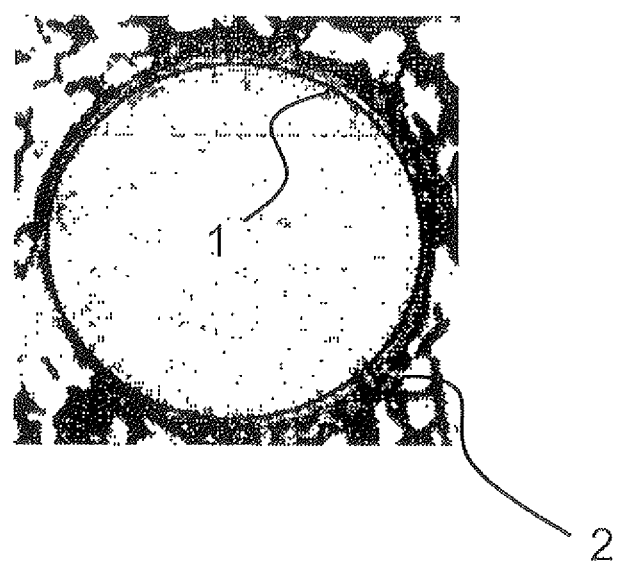

FIG. 1 shows the defect site of the animal that was filled with conventional acrylate-based bone cement; FIG. 2 shows the defect site that was filled with a bone cement according to an example of embodiment of the disclosure.

In order to clearly show the difference, a circle 1 of the same size is superimposed on the two images. This circle 1 could also symbolize an implant, for example. It can be recognized in FIG. 1 that between circle 1 and natural bone material 2, a region 3 is present that is penetrated at most to a small extent by natural bone material. In FIG. 2, the natural bone material 2, in contrast, extends up to circle 1.

It is understood that this example only serves to illustrate the effect of the bone cement according to the disclosure. It can be clearly recognized in the image detail that the natural bone material clearly grows into the bone cement from the side.

Figure 3:
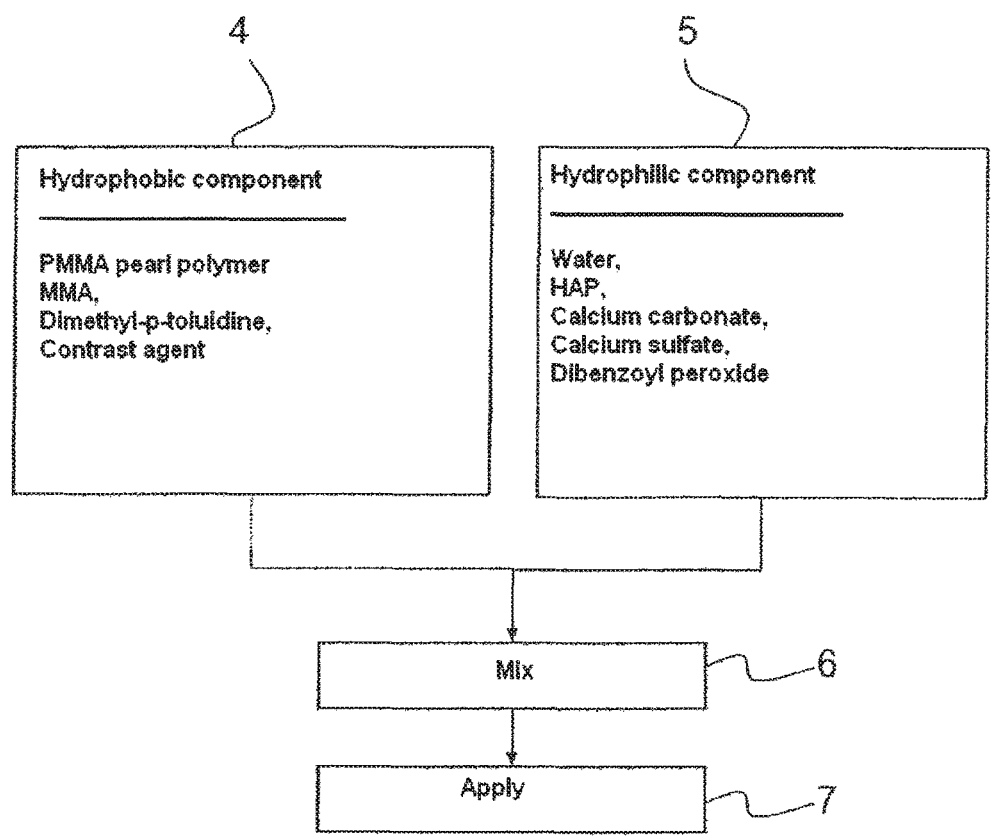
FIG. 3 shows a flow chart of a schematically presented production or mixing method.

Referring to FIG. 3, in this example of an embodiment, the bone cement is mixed from two components, a hydrophobic component 4 and a hydrophilic component 5.

The hydrophobic component comprises a PMMA pearl polymer, methyl methacrylate, dimethyl-p-toluidine as an accelerator and a contrast agent. The hydrophilic component comprises an aqueous suspension containing hydroxyapatite, calcium carbonate, calcium sulfate and, in addition, comprises dibenzoyl peroxide, which is added as an initiator for the polymerization. The two components are mixed in a statistical mixer and can then be applied. The properties of acrylic-based bone cement could be considerably improved by means of the disclosure, depending on the respective use objective.

Figure 4:
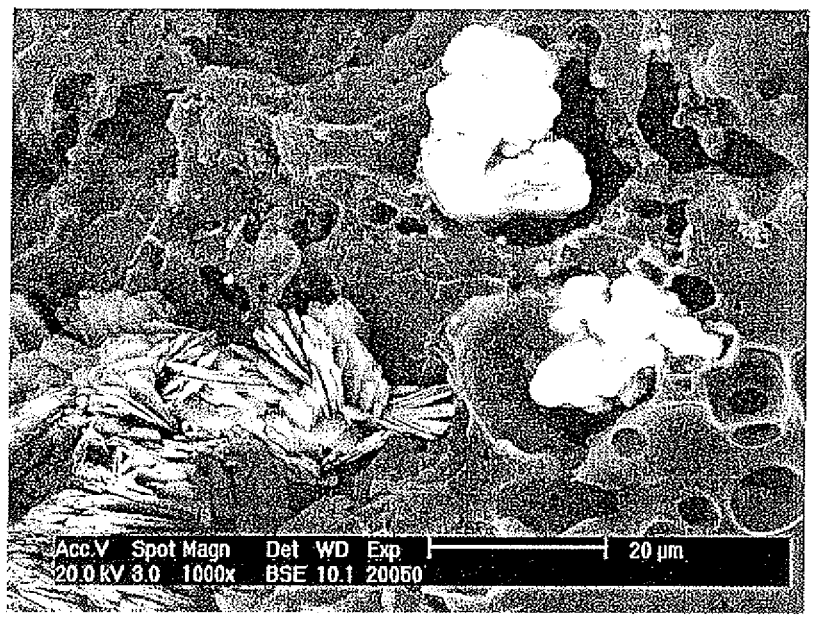
FIGS. 4 to 6 show SEM photomicrographs of a cured bone cement according to the disclosure.
Figure 5:
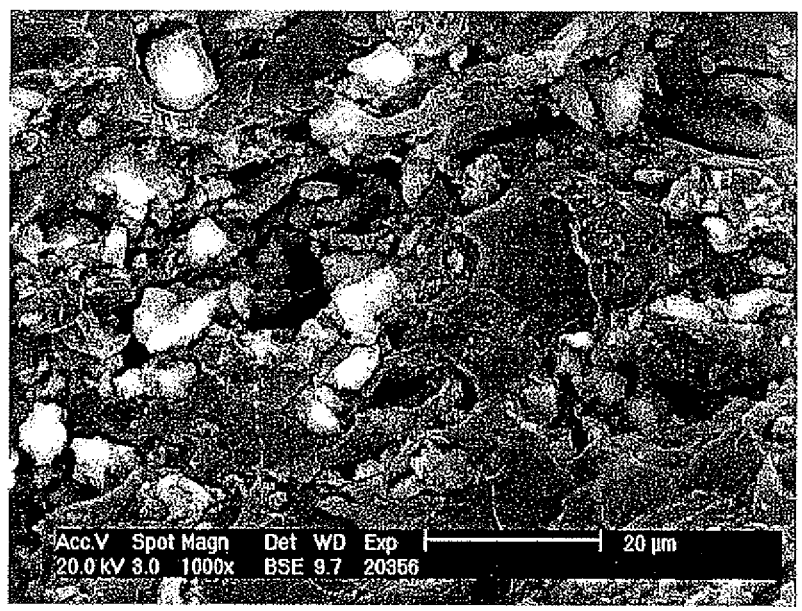
Figure 6:
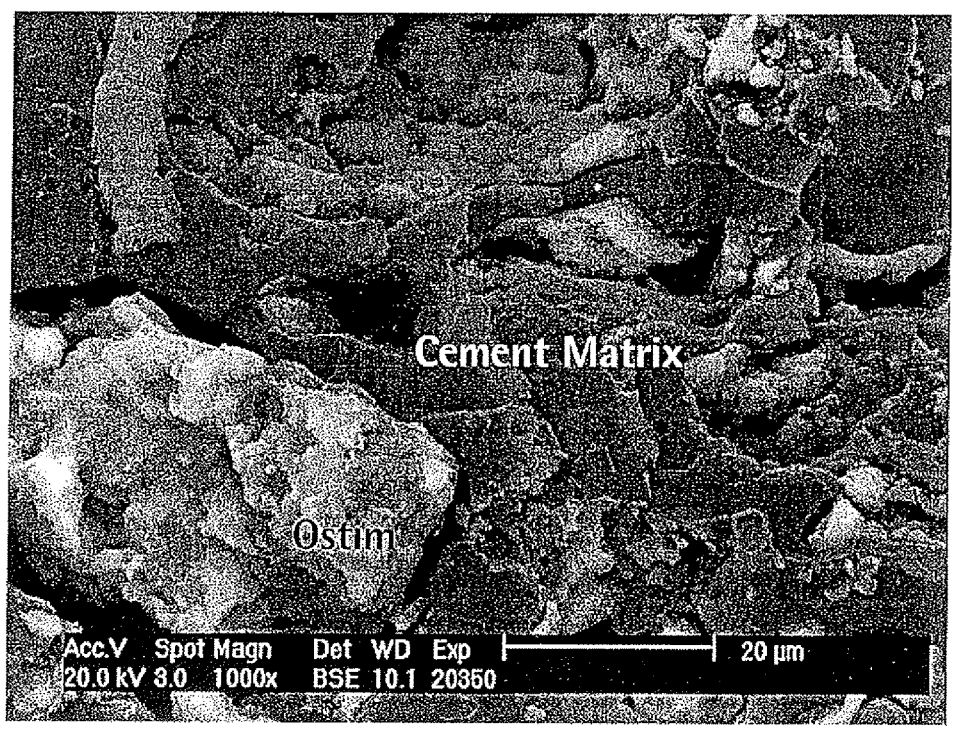

It can be well recognized in FIGS. 4 and 5 that the light particles of hydroxyapatite, which in particular involve nanocrystalline structures that are partially contiguous, are not bound or adhered in the polymer matrix, but that the hydroxyapatite particles are present freely accessible in the pores. It can be recognized in particular that the particles are not densely surrounded by the polymer matrix, but usually only fill a portion of the respective pores. FIG. 6 shows another SEM photomicrograph, in which the polymer matrix is provided with the label "cement matrix" and a hydroxyapatite particle is provided with the label "Ostim".

It is understood that the disclosure is not limited to one combination of the above-described features, but rather that a person skilled in the art will combine all features, as long as this is technically meaningful.

What is claimed is:

1. A method for mixing a bone cement, comprising the steps of:

mixing a hydrophobic component with a hydrophilic, dimension stable paste to form a mixture; and curing the mixture, to form the bone cement, so that the paste forms interconnected open pores within the hydrophobic component, wherein the dimension-stable paste comprises water, an initiator, and biodegradable nanoparticles, wherein at least 50% of the nanoparticles are within the open pores, so that the nanoparticles within the open pores are accessible and not entrapped within the hydrophobic component, wherein the nanoparticles comprise a material selected from the group consisting of calcium carbonate, calcium sulfate, calcium phosphate, hydroxyapatite, and any mixtures thereof, wherein the bone cement comprises 10 to 50 weight % of the nanoparticles, wherein the hydrophobic component is polymerizable, and wherein the polymerizable hydrophobic component is a second paste.

2. The method of claim 1, wherein the second paste comprises an accelerator.

3. The method of claim 1, wherein the second paste comprises polymer particles.

4. The method of claim 1, wherein the hydrophobic component comprises an acrylate.

5. The method of claim 4, further comprising the step of precipitating the acrylate with (meth)acrylic acid, and producing the hydrophobic component with a powder that forms during the precipitating step.

6. The method of claim 4, wherein the acrylate is a metal acrylic salt.

7. The method of claim 1, wherein the dimension stable paste comprises precipitated particles of the nanoparticles.

8. The method of claim 1, wherein particles of the dimension stable paste stick together, thereby forming an interconnected structure.

9. The method of claim 1, wherein the nanoparticles are produced in the same mixture as the hydrophobic component and the hydrophilic and dimension stable paste.

10. The method of claim 1, wherein the nanoparticles have a particles size of 100 nanometers or less.

11. A method for mixing a bone cement, comprising the steps of:
mixing a hydrophobic component with a hydrophilic, dimension stable paste to form a mixture; and
curing the mixture, to form the bone cement, so that the paste forms interconnected open pores within the hydrophobic component,
wherein the dimension-stable paste comprises water, an initiator, and biodegradable nanoparticles,
wherein at least 50% of the nanoparticles are within the open pores, so that the nanoparticles within the open pores are accessible and not entrapped within the hydrophobic component,
wherein the nanoparticles comprise a material selected from the group consisting of calcium carbonate, calcium sulfate, calcium phosphate, hydroxyapatite, and any mixtures thereof,
wherein the bone cement comprises 10 to 50 weight % of the nanoparticles, and
wherein the hydrophobic component comprises an acrylate.

12. A method for mixing a bone cement, comprising the steps of:
mixing a polymerizable hydrophobic component with a hydrophilic, dimension stable paste to form a mixture, and
curing the mixture, to form the bone cement, so that the paste forms interconnected open pores within the hydrophobic component,
wherein the dimension-stable paste comprises water, an initiator, and biodegradable nanoparticles,
wherein at least 50% of the nanoparticles are within the open pores, so that the nanoparticles within the open pores are accessible and not entrapped within the hydrophobic component,
wherein the nanoparticles comprise a material selected from the group consisting of calcium carbonate, calcium sulfate, calcium phosphate, hydroxyapatite, and any mixtures thereof,
wherein the bone cement comprises 10 to 50 weight % of the nanoparticles, and
wherein the dimension stable paste comprises precipitated particles of the nanoparticles.

* * * * *